United States Patent

Boldi et al.

[11] Patent Number: 6,069,248
[45] Date of Patent: May 30, 2000

[54] PROCESS FOR THE SYNTHESIS OF TRIAZOLOPYRIDAZINE COMPOUNDS

[75] Inventors: Armen M. Boldi, Burlingame; Charles R. Johnson, Berkeley, both of Calif.

[73] Assignee: Axys Pharmaceuticals, Inc., South San Francisco, Calif.

[21] Appl. No.: 09/375,803

[22] Filed: Aug. 17, 1999

Related U.S. Application Data

[60] Provisional application No. 60/097,443, Aug. 21, 1998.

[51] Int. Cl.[7] .................................................. C07D 487/04
[52] U.S. Cl. ............................................. 544/236; 544/232
[58] Field of Search ...................................... 544/232, 236

[56] References Cited

U.S. PATENT DOCUMENTS 4,307,094  12/1981  Hassall et al. ........................... 544/236

OTHER PUBLICATIONS

Boldi et al, Chemical Abstracts, vol. 130, abstract 223211, 1999.

*Primary Examiner*—Richard L. Raymond
*Attorney, Agent, or Firm*—Vinit G. Kathardekar

[57] ABSTRACT

The present invention provides a process for the synthesis of triazolopyridazine based compounds represented by Formula A:

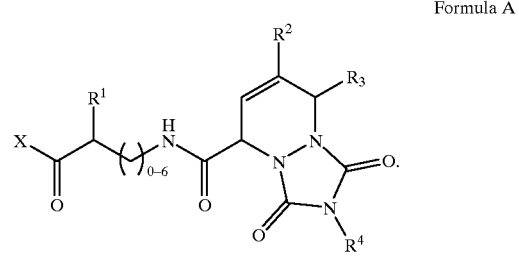

Formula A

These compounds have utility as angiotensin related antihypertensive agents.

13 Claims, No Drawings

PROCESS FOR THE SYNTHESIS OF TRIAZOLOPYRIDAZINE COMPOUNDS

This application claims the benefit under 35 U.S.C Sec. 119 (e)(1) of prior filed U.S. Provisional Application 60/097,443 filed Aug. 21, 1998.

FIELD OF INVENTION

The present invention relates to a process for the synthesis of triazolopyridazine compounds

BACKGROUND OF THE INVENTION

Inhibitors of angiotensin converting enzyme are promising for the control of high blood pressure. One such inhibitor is captopril. Efforts are underway to synthesize compounds which will mimic the inhibitory effects of captopril, but comprising bicyclic systems as reported by Hassall et al., in J. Chem. Soc. Perkins Trans., I, 1984.

One such bicyclic system is represented by compounds comprising the triazolopyridazine skeleton. U.S. Pat. No. 4,307,094 discloses triazolopyridazine derivatives useful as angiotensin related antihypertensive agents.

As discussed above, triazolopyridazine based compounds seem to possess useful biological activity. Efforts continue to make a wider variety of compounds having a triazolopyridazine nucleus. Current synthetic methods useful in making triazolopyridazine derivatives are slow and time consuming. There is thus a need for a new process that will synthesize a plurality of triazolopyridazine compounds in a short amount to time. Such a library of compounds can then be evaluated for its biological activity.

SUMMARY OF INVENTION

Keeping the above discussed needs in mind, the present invention provides a process for the synthesis of a compound of Formula A

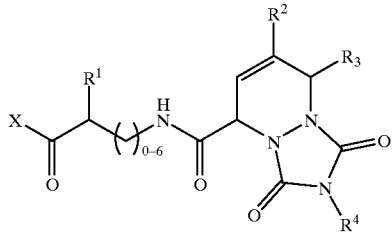

Formula A wherein
$R^1$ represents H, alkyl, substituted alkyl, —OH, —OC$_{1-4}$ alkyl, —N(C$_{1-4}$ alkyl)$_2$, —C$_{1-4}$ alkyl aryl, optionally substituted aryl, or an optionally substituted allyl;
$R^2$ and $R^3$ independently at each occurance represent H, or a group selected from —C$_1$-C$_6$ alkyl, —C$_3$-C$_6$ cycloalkyl aryl, —C$_{2-8}$ alkenyl, —C$_{1-6}$ alkoxy, —C$_{1-4}$ alkyl aryl, and aryl, said group optionally substituted with halogen, —C$_{1-4}$ alkyl, —C$_{1-4}$ alkoxy, allyl, heteroaryl, —SC$_{1-4}$ alkyl, —OC$_{1-4}$ alkyl, —N(C$_{1-4}$ alkyl)$_2$, or benzyl;
$R^4$ represents H or $R^5$;
$R^5$ represents —C$_{4-10}$ branched alkyl or cyclo alkyl, —C$_{1-4}$ alkyl-N(R$^6$)$_2$, —C$_{2-6}$ alkynyl, halo substituted C$_{1-10}$ alkyl, —C$_{2-14}$alkenyl, aryl, C$_{1-8}$ alkyl, heteroaryl, —C$_{1-4}$ alkyl aryl, said —C$_{1-8}$ alkyl, —C$_{2-14}$alkenyl, —C$_{1-4}$ alkyl aryl, and aryl optionally substituted with one to four substituents independently selected from a group consisting of halogen, —C$_1$-C$_6$ alkyl, —C$_{1-6}$ alkoxy, —CF$_3$, —SC$_{1-6}$ alkyl, P(O)(OCH$_3$)$_2$, —S—(CH$_2$)$_{0-4}$ aryl, —O—(CH$_2$)$_{0-4}$ aryl, optionally substituted aryl, optionally substituted heteroaryl, and optionally substituted heterocycloalkyl;
$R^6$ represents —C$_{1-4}$ alkyl, phenyl, H, —C$_{1-4}$ alkyl aryl, and heterocyclyl;
X represents —OH, or —NH$_2$;
the process comprising:
(a) reacting a compound of Formula 2

Formula 2 with a compound of Formula 3

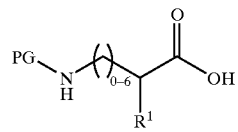

Formula 3 in the presence of a coupling agent,
wherein PG represents an amine protecting group;
X, and $R^1$ are as defined earlier, to yield a compound of Formula 4

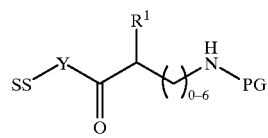

Formula 4 wherein Y represents —NH—, or —O—;
SS represents a solid support; and
$R^1$, and PG are as defined above;
(b) treating a compound of Formula 4 with a deprotecting agent to yield a compound of Formula 5

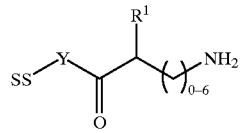

Formula 5 wherein SS, Y, and $R^1$ are as defined above;
(c) reacting the compound of Formula 5 with a compound of Formula 6a

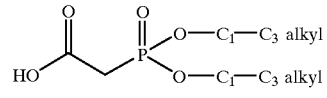

Formula 6a or a compound of Formula 6b

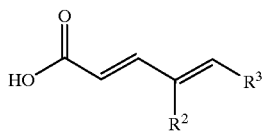

Formula 6b in the presence of a coupling agent,
to yield a compound of Formula 7

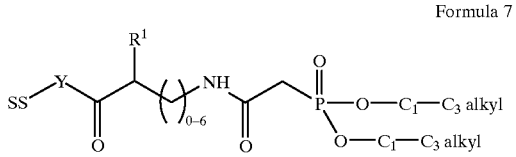

Formula 7 or a compound of Formula 9 respectively

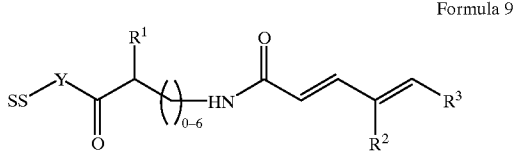

Formula 9 wherein SS, Y, $R^1$, $R^2$, and $R^3$ are as defined above;

(d) reacting a compound of Formula 7 with a compound of Formula 8

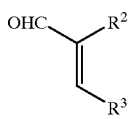

Formula 8 to yield a compound of Formula 9

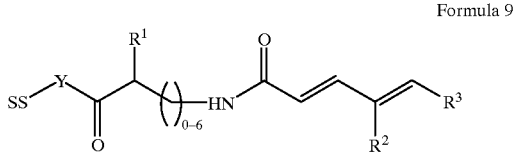

Formula 9 where SS, Y, $R^1$, $R^2$, and $R^3$ are as defined above;

(e) reacting the compound of Formula 9 with a compound of Formula 10

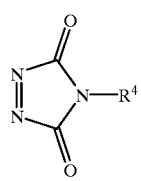

Formula 10 to yield a compound of Formula 11

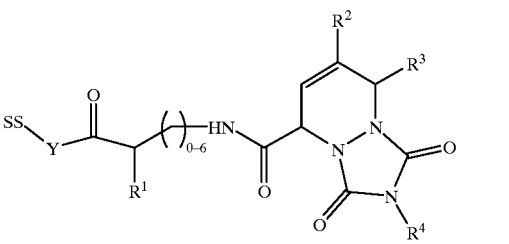

Formula 11 where SS, Y, $R^1$, $R^2$, $R^3$, and $R^4$ are as defined above;

(f) optionally alkylating a compound of Formula 11, wherein $R^4$ is H, with a compound of Formula 12

$R^5$—OH    Formula 12 to yield a compound of Formula 11, wherein $R^4$ is $R^5$; and (g) treating a compound of Formula 11 with a cleaving agent to yield compound of Formula A.

DETAILED DESCRIPTION

Preferred embodiments provide a process wherein $R^1$ represents H, —$C_{1-4}$ alkyl, substituted alkyl, optionally substituted aryl, or —$C_{1-4}$ alkyl aryl; and $R^2$ and $R^3$ independently at each occurance represent H, —$C_1$–$C_4$ alkyl, —$C_{1-4}$ alkyl aryl, or aryl, said alkyl, alkyl aryl, and aryl groups optionally substituted with halogen, —$C_{1-4}$ alkyl, —$SC_{1-4}$ alkyl, —$OC_{1-4}$ alkyl, —$N(C_{1-4}$ alkyl$)_2$, or benzyl.

Another preferred embodiment provides a process wherein the coupling agents in steps (a) and (c) are selected from a group consisting of PyBop, HBTU, TBTU, TNTU, TSTU, HOBT, DIC, DCC, HATU, and HOAT. A further preferred process is one wherein steps (a) and (c) are independently carried out in the presence of a tertiary amine, preferably N-methyl morpholine, or diisopropyl amine, and wherein the coupling agent is PyBop, HOBT, DIC, or DCC.

Yet another preferred embodiment provides a process wherein step (d) comprises a deprotecting agent selected from a group consisting of piperidine, morpholine, dicyclohexyl amine, p-dimethyl aminopyridine, diisopropyl ethyl amine, triethyl amine, and tetrabutyl ammonium fluoride, the preferred deprotecting agent being a 10 to 50% solution of piperidine in DMF, THF, DMA, or DCM. The present invention also provides a process wherein step (d) comprises a basic reagent selected from a group consisting of DBU, DBN, DABCO, triethyl amine, diisopropyl ethyl amine, the preferred basic reagent being DBU; and a solvent selected from a group selected from THF, acetonitrile, dioxane, and DCM, with THF being the preferred solvent.

Other preferred embodiment provides a process wherein step (e) is carried out in the presence of iodobenzene diacetate [PhI(OAc)$_2$], and further wherein when $R^4$=H, step (e) is carried out in the presence of at least one of dioxane and THF. Provided by yet another preferred embodiment is a process wherein step (f) is performed in the presence of DEAD or DIAD; and at least one of triphenylphosphine and tributyl phosphine. Preferred cleaving agents in step (g) of the present process are selected from HCl, and TFA.

The process of the present invention can also be used to prepare a library of compounds of Formula A. Compounds of Formula A were prepared by the process of the present invention, as outlined in Scheme I below.

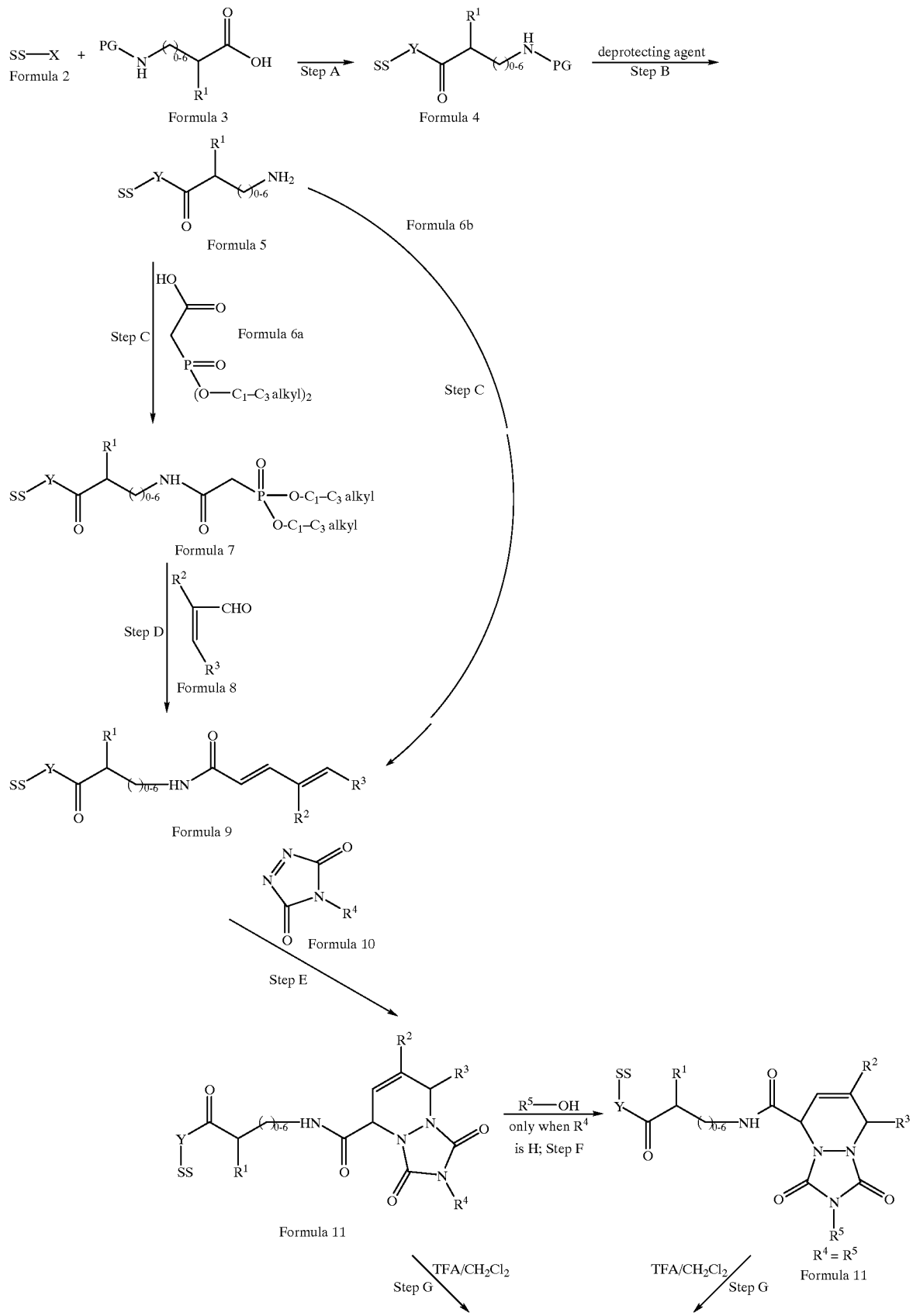
SCHEME I

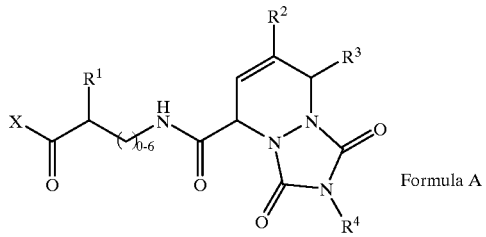

Formula A

EXPERIMENTAL DETAILS
General Procedures

The general process of the present invention is described below. Three different types of washing procedures were used. They are as outlined below.

| Reagent | Amount | Mix Time | Repeat |
|---|---|---|---|
| Wash Cycle 1 | | | |
| 20% Piperidine/DMF | ca. 80 mL | 10 min | 1 |
| 20% Piperidine/DMF | ca. 80 mL | 20 min | 1 |
| DMF | ca. 80 mL | 1 min | 7 |
| Wash Cycle 2 | | | |
| DMF | ca. 80 mL | 1 min | 7 |
| MeOH | ca. 80 mL | 1 min | 2 |
| $Et_2O$ | ca. 80 mL | 1 min | 3 |
| Wash Cycle 3 | | | |
| DMF | ca. 80 mL | 1 min | 7 |

Synthesis of Compounds of Formula 2

Compounds of Formula 2 were prepared as indicated by the following schematic

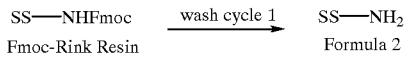

The Fmoc-Rink resin (Advanced ChemTech.) was swelled in DMF for 10 min and then treated by the procedure of Wash Cycle 1.

At this point a positive Kaiser test indicated the deprotection of the amino group of the Fmoc-Rink Resin to yield a compound Formula 2, comprising a free amine group.

Step A: A compound of Formula 2 was treated with a premixed solution of Formula 3, PyBOP, HOBt, and a tertiary amine, preferably NMM (2 to 8 equivalents each) in a minimum amount of an inert solvent. The reaction mixture was mixed for up to 4 h and the reaction was monitored by a Kaiser test. Once the reaction was completed, as indicated by a negative Kaiser test suggesting disappearance of a free amino group containing compound of Formula 2, the solvent was drawn off under vacuum and the resulting resin residue was washed as described in Wash Cycle 2 or Wash Cycle 3, and dried under reduced pressure to yield a compound of Formula 4.

Step B: Deprotection of Fmoc-Amino Acid-Rink Resin: A compound of Formula 4 was swelled in an inert solvent, preferably DMF for up to 30 min and then treated with a deprotecting agent, preferably as described in Wash Cycle 1. At this point a positive Kaiser test indicated the formation of a compound of Formula 5, i.e., a compound containing a free amine group.

Step C: A compound of Formula 5 was treated with a premixed solution of a compound of Formula 6a or 6b, PyBOP, HOBt, and a tertiary amine (2–8 equivalent each), in a minimum amount of an inert solvent, preferably DMF for dissolution. The reaction mixture was mixed for up to 6 h. The reaction was monitored using the Kaiser test, as in Step A. The solvent was removed under vacuum, residue was washed as described in Wash Cycle 2, followed by drying under reduced pressure to yield a compound of Formula 7 or Formula 9 respectively.

Step D: A compound of Formula 7 was dissolved in a minimum amount of an inert solvent, preferably THF, in a reaction flask, optionally in the presence of LiBr, LiCl, $MgBr_2$, or MgCl, or mixtures thereof. A freshly prepared solution of DBU in an inert solvent, and a solution of an aldehyde, a compound of Formula 8, were added to the reaction flask. The reaction mixture was stirred for up to 4 h, followed by washing with water, MeOH, and DCM. The washed reaction residue was dried under reduced pressure to yield a compound of Formula 9.

Step E (When $R^4=R^5$): An urazole, a compound of Formula 10, and iodobenzenediacetate were placed in an inert solvent, preferably DMF, forming a reaction mixture. The reaction mixture was mixed in the dark for up to 30 min and added to compound of Formula 9. The reaction vessel was sealed and the reaction mixture was washed for up to 24 h. The resulting resin was formed with a mixture of DMF and MeOH, followed by DCM. The solvents were removed to yield a compound of Formula 11.

Step E (When $R^4=RH$): To a compound of Formula 9 was added a minimum amount of an inert solvent, preferably dioxane necessary to swell the compound of Formula 9, followed by the addition of urazole. After mixing the above, a dioxane solution of iodobenzenediacetate was added in 4 equal portions over 4 h, with stirring. After overnight standing the reaction mixture was washed with DMF, MeOH, and DCM. This process yielded a compound of Formula 11.

Step F: In an inert solvent was placed a compound of Formula 11, at least one of triphenyl phosphine or tributyl phosphine, a compound of Formula 12, and DEAD. This mixture was stirred overnight resulting in the formation of a resin. The resulting resin was rinsed with DMF, MeOH, and DCM to yield a compound of Formula 13.

Step G: A compound of Formula 11, or Formula 13, was treated with a 1:1 mixture of DCM:TFA for up to 30 minutes. Alternatively, a compound of Formula 11, or Formula 13, can be washed with a 1:1 mixture of DCM:TFA. In either case the respective procedures yielded a compound of Formula A.

Examples 1–12 were prepared using the following procedures:

Step A: A compound of Formula 2 (1 eq.) was treated with a premixed solution of Formula 3, PyBOP, HOBt, and NMM (4.0 equivalents each) in a minimum amount of DMF for dissolution. The reaction mixture was mixed via $N_2$ bubbling for 2 h and the reaction was monitored by a Kaiser test.

Once the reaction was completed, as indicated by a negative Kaiser test suggesting disappearance of a free amino group containing compound of Formula 2, DMF, was drawn off under vacuum and the resin was washed as described in Wash Cycle 2, or Wash Cycle 3. The resin was dried under reduced pressure to yield a compound of Formula 4.

Step B: Deprotection of Fmoc-Amino Acid-Rink Resin. A compound of Formula 4 was placed in a reaction vessel equipped with a nitrogen/vacuum manifold. A compound of Formula 4 was swelled in DMF for 10 min and then treated with a deprotecting agent as described in Wash Cycle 1. At this point a positive Kaiser test indicated the formation of a compound of Formula 5, i.e., a compound containing a free amine group.

Step C: A compound of Formula 5 (1 equivalent), was treated with a premixed solution of a compound of Formula 6a or 6b, PyBOP, HOBt, and NMM (4.0 equivalent each), in a minimum amount of an inert solvent, preferably DMF for dissolution. The reaction mixture was mixed via $N_2$ bubbling for 2 h. The reaction was monitored using the Kaiser test, as described in Step A. DMF was removed under vacuum and the residue was washed as described in Wash Cycle 2, followed by drying under reduced pressure to yield compounds of Formula 7 and Formula 9 respectively.

Step D: A compound of Formula 7 (1 equivalent), and solid LiBr (0–15 equivalents), were dissolved in a minimum amount of THF, and placed in a reaction flask. A freshly prepared solution of DBU in THF (1 M, 1 mL), and a solution of an aldehyde, a compound of Formula 8 in THF (2 M) was then added to the reaction flask. The reaction mixture was stirred for up to 4 h, followed by washing it with water, MeOH, and DCM. This washed reaction residue was then dried under reduced pressure to yield a compound of Formula 9.

Step E (When $R^4=R^5$): An urazole, a compound of Formula 10, (0.4 mmol) and iodobenzenediacetate (0.4 mmol) were placed in DMF, forming a reaction mixture. The reaction mixture was mixed in the dark for 15 min and immediately added to a compound of Formula 9. The reaction vessel was sealed and the reaction mixture was mixed for up to 24 h. The resulting resin was washed with a mixture of DMF and MeOH, followed by DCM. The solvents were removed to yield a compound of Formula 11.

Step E (When $R^4=H$): To a compound of Formula 9 (3.25 mmol) was added a minimum amount of dioxane necessary to swell the compound of formula 9, followed by urazole (12–18 mmol). After mixing the above, a dioxane solution of iodobenzenediacetate (about 15–20 mmol) was added in 4 equal portions over four hours with stirring. After overnight standing the reaction mixture was washed with DMF, MeOH, and DCM. This process yielded a compound of Formula 11.

Step F: In a reaction vessel was placed an inert solvent or mixtures thereof, preferably THF. To this were added a compound of Formula 11 (0.1 mmol), and a solution of triphenylphosphine in an inert solvent, preferably THF (0.4–1.2 mmol) and a freshly prepared solution of a compound of Formula 12 (0.6–2 mmol), and DEAD in two equal portions (0.2–0.6 mmol each). This resulting solution was stirred overnight. The resulting resin was washed with DMF, MeOH, and DCM to yield a compound of Formula 13.

Steps G: A compound of Formula 11 was treated with a 1:1 mixture of DCM:TFA for up to 30 minutes. Alternatively, a compound of Formula 11, or Formula 13, can be washed with a 1:1 mixture of DCM:TFA. In either case the respective procedures yielded a compound of Formula A.

The following examples were made using the process of the present invention:

EXAMPLE 1

$R^1$=H; $R^2$=—$C_3H_7$; $R^3$=—$C_4H_9$; $R^4$=H; and X=—$NH_2$; Molecular Formula: $C_{20}H_{33}N_5O_4$; Molecular Weight: 407.51; MS (ESI) m/z 408 [(M+H)$^+$].

EXAMPLE 2

$R^1$=—$CH_3$; $R^2$=H; $R^3$=—$CH_3$; $R^4$=—$CH_3$; and X=—$NH_2$; Molecular Formula: $C_{12}H_{17}N_5O_4$; Molecular Weight: 295.29; $^1$H NMR (270 MHz, CDCl$_3$) δ7.13–7.01 (m, 1 H), 6.57–6.54 (m, 1 H), 5.91–5.86 (m, 3 H), 4.70–4.69 (m, 1 H), 4.60–4.41 (m, 2 H), 3.11 (s, 3 H), 3.09 (s 3 H), 2.06 (s, 3 H), 1.49 (d, J=6.7 Hz, 3 H), 1.42 (d, J=6.7 Hz, 3 H). MS (ESI) m/z 296 [(M+H)$^+$].

EXAMPLE 3

R1=—$CH_3$; $R^2$=H; $R^3$=—Ph; $R^4$=—$CH_3$; and X=—$NH_2$; (1:1 mixture of diastereomers); Molecular Formula: $C_{17}H_{19}N_5O_4$; Molecular Weight: 357.36; $^1$H NMR (270 MHz, CD$_3$CN) δ7.50–7.32 (m, 5 H), 6.91 (bs, 1 H), 6.07 (d, 1 H), 5.99 (d, 1 H), 5.89 (bs, 1 H), 5.54–5.53 (m, 1 H), 5.41–5.40 (m, 1 H), 4.86–4.85 (m, 1 H), 4.81–4.80 (m, 1 H), 4.36–4.30 (m, 1 H), 2.93 (s, 3 H), 2.89 (s, 3 H), 1.37 (s, 3 H), 1.34 (s, 3 H). MS (ESI) m/z 358 [(M+H)$^+$].

EXAMPLE 4

$R^1$=—$CH_3$; $R^2$=H; $R^3$=—Ph; $R^4$=—Ph; and X=—$NH_2$; (2:1 mixture of diastereomers); Molecular Formula: $C_{22}H_{21}N_5O_4$; Molecular Weight: 419.43; $^1$H NMR (270 MHz, CDCl$_3$) δ7.60–7.24 (m, 10 H), 6.95 (s, 1 H), 6.68 (d, J=7.7 Hz, 1 H), 6.39 (d, J=10.1 Hz, 1 H), 6.22 (d, 2 H), 6.09–5.94 (m, 2 H), 5.77 (d, 1 H), 5.50 (bs, 1 H), 5.21 (bs, 3 H), 4.93 (d, 2 H), 4.63–4.51 (m, 2 H), 1.45 (d, J=7.4 Hz, 3 H). MS (ESI) m/z 420 [(M+H)$^+$].

EXAMPLE 5

$R^1$=—$CH_2Ph$; $R^2$=H; $R^3$=—Ph; $R^4$=—Ph; and X=—$NH_2$; (1:1 mixture of diastereomers); Molecular Formula: $C_{28}H_{25}N_5O_4$; Molecular Weight: 495.53; $^1$H NMR (270 MHz, CD$_3$OD/CDCl$_3$) δ7.70–7.32 (m, 13 H), 7.05–7.02 (m, 2 H); 6.27–6.21 (d, 2 H), 4.89–4.87 (m, 1 H), 3.48 (d, 2 H), 3.40–3.31 (m, 1 H), 3.15–3.08 (m, 1 H). MS (ESI) m/z 496 [(M+H)$^+$].

EXAMPLE 6

$R^1$=H; $R^2$=H; $R^3$=—$CH_3$; $R^4$=—$CH_3$; and X=—$NH_2$; Molecular Formula: $C_{12}H_{17}N_5O_4$; Molecular Weight: 295.29; $^1$H NMR (270 MHz, CDCl$_3$) δ6.08 (bs, 1 H), 5.96 (bs, 1 H), 5.90 (d, 2 H), 4.79 (bs, 1 H), 4.47–4.42 (m, 1 H), 3.57–3.51 (m, 2 H), 3.07 (s, 3 H), 2.49–2.44 (m, 2 H), 1.99 (s, 1 H), 1.51–1.49 (d, J=6.4 Hz, 3 H). MS (ESI) m/z 296 [(M+H)$^+$].

EXAMPLE 7

$R^1$=H; $R^2$=H; $R^3$=—$CH_3$; $R^4$=—Ph; and X=—$NH_2$; Molecular Formula: $C_{17}H_{19}N_5O_4$; Molecular Weight: 357.36; $^1$H NMR (270 MHz, CDCl$_3$) δ7.47–7.35 (m, 5 H), 7.24–7.15 (m, 1 H), 6.34 (bs, 2 H), 5.94–5.80 (m, 2 H), 5.57 (bs, 1 H), 4.83 (bs, 1 H), 4.53 (bs, 1 H), 3.54–3.50 (m, 2 H), 2.43 (bs, 2 H), 1.56 (d, J=6.7 Hz, 3 H). MS (ESI) m/z 358 [(M+H)$^+$].

EXAMPLE 8

$R^1$=H; $R^2$=H; $R^3$=—Ph; $R^4$=—(CH$_2$)$_2$-phenoxy; and X=—$NH_2$; Molecular Formula: $C_{24}H_{25}N_5O_5$; Molecular Weight: 463.49; MS (ESI) m/z 464 [(M+H)$^+$].

EXAMPLE 9

$R^1$=H; $R^2$=Ph; $R^3$=—i-propyl; $R^4$=—$(CH_2)_2$-butoxy; and X=—$NH_2$; Molecular Formula: $C_{25}H_{35}N_5O_5$; Molecular Weight: 485.58; $^1$H NMR (270 MHz, $CD_3OD$) δ8.50–8.46 (t, J=5.5 Hz, 1 H), 7.47–7.39 (m, 5 H), 6.10 (d, 4.0 Hz, 1 H), 5.20 (d, J=3.2 Hz, 1 H), 5.08 (d, J=4.5 Hz, 1 H), 3.83–3.72 (m, 2 H), 3.70–3.60 (m, 2 H), 3.47–3.35 (m, 4 H), 3.30 (d, J=1.5 Hz, 2 H), 3.29 (d, J=1.5 Hz, 2 H), 2.37 (t, J=6.7 Hz, 2 H), 2.03–1.97 (m, 1 H), 1.55–1.48 (m, 2 H), 1.37–1.28 (m, 2 H), 0.97–0.75 (m, 10 H). MS (ESI) m/z 486 [(M+H)$^+$].

EXAMPLE 10

$R^1$=—H; $R^2$=$C_3H_7$; $R^3$=—$C_4H_9$; $R^4$=—$(CH_2)_2$-butoxy; and X=—$NH_2$; Molecular Formula: $C_{23}H_{39}N_5O_5$; Molecular Weight: 465.59; $^1$H NMR (270 MHz, $CD_3OD$) δ5.68 (d, J=3.5 Hz, 1 H), 4.73–4.72 (m, 1 H), 4.44 (bs, 1 H), 3.80–3.60 (m, 4 H), 3.48–3.40 (m, 4 H), 3.32–3.29 (m, 3 H), 2.46–2.35 (m, 2 H), 2.15–1.20 (m, 14 H), 0.95–0.85 (m, 10 H). MS (ESI) m/z 466 [(M+H)$^+$].

EXAMPLE 11

$R^1$=—H; $R^2$=H; $R^3$=—Ph; $R^4$=—$(CH_2)_2$-cyclohexyl; and X=—$NH_2$; Molecular Formula: $C_{24}H_{31}N_5O_4$; Molecular Weight: 453.53; $^1$H NMR (270 MHz, $CDCl_3$) δ6 8.42 (bs, 1 H), 7.50–7.25 (m, 5 H), 6.01–5.99 (m, 2 H), 5.42 (bs, 1 H), 3.58–3.41 (m), 3.36–3.23 (m), 2.50–2.45 (t, J=6.9 Hz, 2 H), 1.80–1.56 (m), 1.49–1.35 (m), 1.28–1.08 (m), 0.95–0.75 (m,). MS (ESI) m/z 454 [(M+H)$^+$].

EXAMPLE 12

$R^1$=—$CH_2$—O—$CH_2$—Ph; $R^2$=H; $R^3$=pOMe—Ph; $R^4$=—$(CH_2)_2$-2-pyridyl; and X=—$NH_2$; Molecular Formula: $C_{31}H_{32}N_6O_6$; Molecular Weight: 584.62; $^1$H NMR (270 MHz, $CDCl_3$) δ8.80–8.51 (m, 2 H), 8.29–8.25 (m, 1 H), 7.81–7.71 (m, 2 H), 7.33–7.20 (m, 6 H), 6.91–6.86 (d, J=7.9 Hz, 2 H), 6.22–5.87 (m, 2 H), 5.42–5.01 (m, 2 H), 4.60–4.51 (m, 3 H), 3.92–3.72 (m, 8 H), 3.31–3.20 (m, 15 H). MS (ESI) m/z 585 [(M+H)$^+$].

Analytical Methods:

Mass spectra were obtained for compounds of Formula A. Mass spectra were obtained by conventional methods known to one skilled in the art.

DEFINITIONS AND ABBREVIATIONS

As used in the present invention the following terms and abbreviations have the following meaning, unless otherwise indicated.

Library of compounds: This term indicates a collection of independent (individual) compounds that are synthesized by the process of the present invention. Generally the term library of compounds indicates a collection of individual compounds distinct from one another. Also included in the library of compounds is a mixture of the individual compounds.

"Alkyl", or "alkyl radical" is meant to indicate a hydrocarbon moiety of up to 14 carbon atoms, unless indicated otherwise. This hydrocarbon is generally attached to at least one other atom, and can be straight chain, or branched, or cyclic, or a combination thereof. The term "straight chain alkyl" is meant to represent an unbranched hydrocarbon moiety of up to 8 carbon atoms. An example of a straight chain alkyl is a n-pentyl group. The term "alkylene" represents an alkyl group, as defined above, except that it has at least one center of unsaturation, i.e., a double bond. Illustrative examples are butene, propene, and pentene.

The term "alkoxy" as used herein represents —$OC_{1-6}$ alkyl. The term "cycloalkyl", "cycloalkyl ring", "cycloalkyl radical" or "cyclic hydrocarbon" indicates a saturated or partially unsaturated three to fourteen carbon monocyclic or bicyclic hydrocarbon moiety which is optionally substituted with an alkyl group.

The term "aryl" means an aromatic monocyclic, bicyclic, or a fused polycyclic hydrocarbon radical containing from 6 to 14 carbon atoms or the number indicated. Thus a $C_6$–$C_{1-4}$ aryl group includes phenyl, naphthyl, anthracenyl, etc. The term "heteroaryl" means aryl, as defined above, containing 5–14 atoms wherein one or more of the carbon atoms is replaced by a hetero atom chosen from N, O, and S. The hetero atoms can exist in their chemically allowed oxidation states. Thus Sulfur (S) can exist as a sulfide, sulfoxide, or sulfone. Illustrative examples of heteroaryl groups are thienyl, N-substituted succinimide, 3-(alkyl amino)-5,5-dialkyl-2-cyclohexen-1-one, methyl pyridyl, alkyl theophylline, furyl, pyrrolyl, indolyl, pyrimidinyl, isoxazolyl, purinyl, imidazolyl, pyridyl, pyrazolyl, quinolyl, and pyrazinyl. The term "heterocycloalkyl" means a cyclo alkyl group containing from 5 to 14 carbon atoms wherein one or more of the carbon atoms is replaced by a hetero atom chosen from N, O, and S. The hetero atoms can exist in their chemically allowed oxidation states. Thus Sulfur (S) can exist as a sulfide, sulfoxide, or sulfone. The heterocycloalkyl group can be completely saturated or partially unsaturated. Illustrative examples are piperidine, 1,4-dioxane, and morpholine.

"Optional substituents" for alkyl, aryl, heterocycloalkyl, and hetero aryl groups are independently selected from a group consisting of H, —$NH_2$, halo, —$SC_{1-4}$ alkyl, —S aryl, —O—$C_{1-4}$ alkyl, —$NHC_1$–$C_4$ alkyl, —$N(C_1$–$C_4)_2$ alkyl, $CF_3$, and $C_{1-4}$ alkyl.

"Optional" or "optionally" means that the subsequently described event or circumstance may or may not occur, and that the description includes instances where the event or circumstance occurs and instances in which it does not. For example, the phrase "optionally is substituted with one to three substituents" means that the group referred to may or may not be substituted in order to fall within the scope of the invention.

The term "deprotecting agent" is used to mean an agent which selectively removes a PG from a functional group such as an amine group in step (b), as long as in the present case it does not cleave the SS-Y bond. The deprotecting agent can be an acidic or basic moiety as understood by one skilled in the art. The term "protecting group" or "PG", as used herein, indicates a group that protects an amine functional group rendering the amine inactive. A detailed description of the terms "deprotecting agent", and "protecting group" (PG) is available in Protective Groups in Organic Synthesis, 2nd edition, T. W. Greene and P. G. M. Wuts, 1991, which is incorporated herein by reference.

As used herein, "cleaving agent" typically represents an acid which cleaves a compound of Formula A from the SS. Illustrative examples are TFA, and HCl. The "Kaiser" test is used to detect a free primary or secondary amine. Details of the Kaiser test are described in Kaiser et al., Anal Biochem, 1970, Vol. 34, pg. 595–598.

The term "solid support" (SS), as used in the present invention, signifies polymeric material for supported synthesis. In the instant case it is understood that SS includes a "linker molecule". A detailed description of the terms linker molecule, and solid support can be found in The Combinatorial Index, B. A. Bunin, 1998, which is incorporated herein by reference.

The term "halo" or "halogen" represents at least one of chlorine, bromine, iodine, and fluorine radicals. "Inert solvent" as used herein represents solvents which do not react with the reagents dissolved therein. Illustrative examples of inert solvents are tetrahydrofuran (THF), methylene chloride, dichloro methane (DCM), ethyl acetate (EtOAc), dimethyl formamide (DMF), diaoxane, chloroform, and DMSO.

Abbreviations:
AcOH=Acetic acid
ACN=Acetonitrile
BOC=t-Butoxycarbonyl
DBU=1,8-Diazabicyclo[5.4.0]undec-7-ene
DCM=Dichloromethane
DMF=N,N-Dimethylformamide
Fmoc=9-Fluorenylmethoxycarbonyl
HOBT=1-Hydroxybenzotriazole
MS=Mass spectroscopy
NMM=N-Methyl morpholine
PyBOP=Benzotriazole-1-yl-oxy-tris-pyrrolidino-phosphonium hexafluorophosphate
TFA=Trifluoroacetic acid
THF=Tetrahydrofuran
MeOH=methanol
DEAD=Diethyl azodicarboxylate
TBTU=2-(1H-Benzotriazole-1-yl)-1,1,3,3-tetramethyluronium tetrafluoroborate
TNTU=2-(5-Norbornene-2,3-dicarboximido)-1,1,3,3-tetramethyluronium tetrafluoroborate
TSTU=O-(N-Succinimidyl)-1,1,3,3-tetramethyluronium tetrafluoroborate
DIC=Diisopropylcarbodiimide
DCC=Dicyclohexylcarbodiimide
HATU=N-{(dimethylamino)(1H-1,2,3-triazolo[4,5-b]pyridin-1-yl)-methylene}-N-methylmethanaminium hexafluorophosphate N-oxide
HOAt=1-hydroxy-7-azabenzotriazole
BOP=Benzotriazol-1-yloxy-tris(dimethylamino)phosphonium hexafluorophosphate
HBTU=2-(1H-Benzotriazole-1-yl)-1,1,3,3-tetramethyluronium hexafluorophosphate
PyBrOP=Bromo-tris-pyrrolidino-phosphonium hexafluorophosphate

We claim:

1. A process for the synthesis of a compound of Formula A:

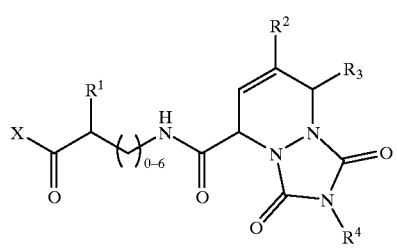

Formula A wherein
R$^1$ represents H, alkyl, substituted alkyl, —OH, —OC$_{1-4}$ alkyl, —N(C$_{1-4}$ alkyl)$_2$, —C$_{1-4}$ alkyl aryl, optionally substituted aryl, or an optionally substituted allyl;
R$^2$ and R$^3$ independently at each occurance represent H, or a group selected from —C$_1$–C$_6$ alkyl, —C$_3$–C$_6$ cycloalkyl aryl, —C$_{2-8}$ alkenyl, —C$_{1-6}$ alkoxy, —C$_{1-4}$ alkyl aryl, and aryl, said group optionally substituted with halogen, —C$_{1-4}$ alkyl, —C$_{1-4}$ alkoxy, allyl, heteroaryl, —SC$_{1-4}$ alkyl, —OC$_{1-4}$ alkyl, —N(C$_{1-4}$ alkyl)$_2$, or benzyl;
R$^4$ represents H or R$^5$;
R$^5$ represents C$_{4-10}$ branched alkyl or cyclo alkyl, —C$_{1-4}$ alkyl-N(R$^6$)$_2$, —C$_{2-6}$ alkynyl, halo substituted C$_{1-10}$ alkyl, —C$_{2-4}$alkenyl, aryl, —C$_{1-8}$ alkyl, heteroaryl, —C$_{1-4}$ alkyl aryl, said —C$_{1-8}$ alkyl, —C$_{2-14}$alkenyl, —C$_{1-4}$ alkyl aryl, and aryl optionally substituted with one to four substituents independently selected from a group consisting of halogen, —C$_1$–C$_6$ alkyl, —C$_{1-6}$ alkoxy, —CF$_3$, —SC$_{1-6}$ alkyl, P(O)(OCH$_3$)$_2$, —S—(CH$_2$)$_{0-4}$ aryl, —O—(CH$_2$)$_{0-4}$ aryl, optionally substituted aryl, optionally substituted heteroaryl, and optionally substituted heterocycloalkyl;
R$^6$ represents —C$_{1-4}$ alkyl, phenyl, H, —C$_{1-4}$ alkyl aryl, and heterocyclyl;
X represents —OH, or —NH$_2$;
the process comprising:
(a) reacting a compound of Formula 2

SS—X                              Formula 2 with a compound of Formula 3

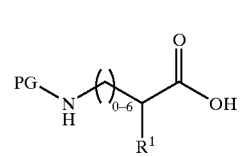

Formula 3 in the presence of a coupling agent,
wherein PG represents an amino protecting group;
X, and R$^1$ are as defined earlier,
to yield a compound of Formula 4

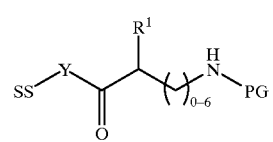

Formula 4 wherein Y represents —NH—, or —O—;
SS represents a solid support; and
R$^1$, and PG are as defined above;
(b) treating a compound of Formula 4 with a deprotecting agent to yield a compound of Formula 5

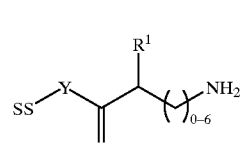

Formula 5 wherein SS, Y, and R$^1$ are as defined above;
(c) reacting the compound of Formula 5 with a compound of Formula 6a Formula 6a

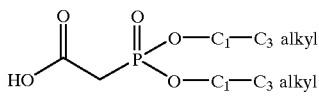

or a compound of Formula 6b

Formula 6b

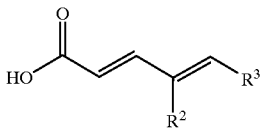

in the presence of a coupling agent, to yield a compound of Formula 7

Formula 7

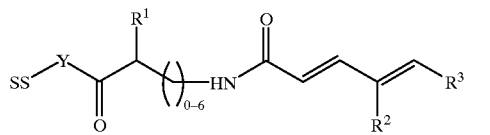

or a compound of Formula 9 respectively

Formula 9

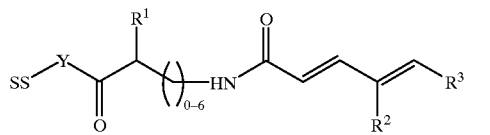

wherein SS, Y, $R^1$, $R^2$, and $R^3$ are as defined above;

(d) reacting a compound of Formula 7 with a compound of Formula 8

Formula 8

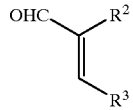

to yield a compound of Formula 9

Formula 9

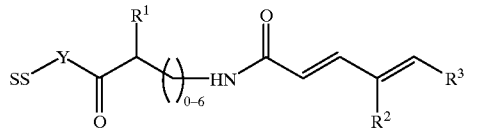

where SS, Y, $R^1$, $R^2$, and $R^3$ are as defined above;
(e) reacting the compound of Formula 9 with a compound of Formula 10

Formula 10

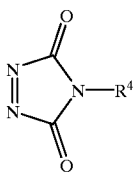

to yield a compound of Formula 11

Formula 11

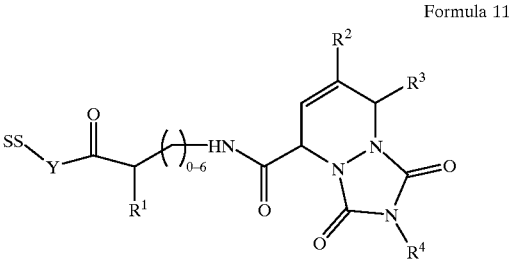

where SS, Y, $R^1$, $R^2$, $R^3$, and $R^4$ are as defined above;
(f) optionally alkylating a compound of Formula 11, wherein $R^4$ is H, with a compound of Formula 12

$$R^5\text{—OH} \qquad \text{Formula 12}$$

to yield a compound of Formula 11, wherein $R^4$ is $R^5$; and (g) treating a compound of Formula 11 with a cleaving agent to yield compound of Formula A.

2. A process of claim 1 wherein:

$R^1$ represents H, —$C_{1-4}$ alkyl, substituted alkyl, optionally substituted aryl, or —$C_{1-4}$ alkyl aryl; and $R^2$ and $R^3$ independently at each occurance represent H, —$C_1$-$C_4$ alkyl, —$C_{1-4}$ alkyl aryl, or aryl, said alkyl, alkyl aryl, and aryl groups optionally substituted with halogen, —$C_{1-4}$ alkyl, —$SC_{1-4}$ alkyl, —$OC_{1-4}$ alkyl, —$N(C_{1-4}$ alkyl$)_2$, or benzyl.

3. A process of claim 2 wherein the coupling agents in steps (a) and (c) are selected from a group consisting of PyBop, HBTU, TBTU, TNTU, TSTU, HOBT, DIC, DCC, HATU, and HOAT.

4. A process of claim 3 wherein steps (a) and (c) are independently carried out in the presence of a tertiary amine.

5. A process of claim 4 wherein the coupling agent is PyBop, HOBT, DIC, or DCC; and the tertiary amine is N-methyl morpholine, or diisopropyl amine.

6. A process of claim 3 wherein step (d) comprises a deprotecting agent selected from a group consisting of piperidine, morpholine, dicyclohexyl amine, p-dimethyl aminopyridine, diisopropyl ethyl amine, triethyl amine, and tetrabutyl ammonium fluoride.

7. A process of claim 6 wherein the deprotecting agent is a 10 to 50% solution of piperidine in DMF, THF, DMA, or DCM.

8. A process of claim 3 wherein step (d) comprises a basic reagent selected from a group consisting of DBU, DBN, DABCO, triethyl amine, diisopropyl ethyl amine; and
a solvent selected from a group selected from THF, acetonitrile, dioxane, and DCM.

9. A process of claim 8 wherein the basic reagent is DBU, and the solvent is THF.

10. A process of claim 3 wherein step (e) is carried out in the presence of iodobenzene diacetate [PhI(OAc)$_2$].

11. A process of claim 10 wherein when $R^4$=H, step (e) is carried out in the presence of at least one of dioxane and THF.

12. A process of claim 3 wherein step (f) is performed in the presence of DEAD or DIAD; and
   at least one of triphenylphosphine and tributyl phosphine.

13. A process of claim 3 wherein the cleaving agent in step (g) is selected from HCl, and TFA.

* * * * *

UNITED STATES PATENT AND TRADEMARK OFFICE
CERTIFICATE OF CORRECTION

PATENT NO. : 6,069,248
DATED : May 30, 2000
INVENTOR(S) : Armen M. Boldi, Charles R. Johnson It is certified that error appears in the above-identified patent and that said Letters Patent are hereby corrected as shown below:

Column 14
Line 10 (of Claims): Delete --tour-- and replace with --four-- therefore.

Signed and Sealed this

Twenty-seventh Day of March, 2001

Attest:

NICHOLAS P. GODICI

Attesting Officer

*Acting Director of the United States Patent and Trademark Office*